(12) United States Patent
Villanueva

(10) Patent No.: US 7,179,481 B2
(45) Date of Patent: Feb. 20, 2007

(54) VAGINAL HEALTH PRODUCTS

(75) Inventor: Julie M. Villanueva, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 608 days.

(21) Appl. No.: 10/247,799

(22) Filed: Sep. 19, 2002

(65) Prior Publication Data

US 2004/0063787 A1    Apr. 1, 2004

(51) Int. Cl.
    *A61F 2/02*    (2006.01)
(52) U.S. Cl. ...................................... 424/423
(58) Field of Classification Search ............... 424/423
    See application file for complete search history.

(56) References Cited

U.S. PATENT DOCUMENTS

| | | | |
|---|---|---|---|
| 5,352,699 A | 10/1994 | Jackson | |
| 5,789,391 A | 8/1998 | Jacobus et al. | 514/51 |
| 5,837,861 A | 11/1998 | Pendergast et al. | 536/25.6 |
| 5,958,897 A | 9/1999 | Jacobus et al. | 514/49 |
| 5,972,904 A | 10/1999 | Jacobus et al. | 514/51 |
| 5,981,506 A | 11/1999 | Jacobus et al. | 514/47 |
| 5,985,849 A | 11/1999 | Kindon et al. | 514/51 |
| 6,107,091 A | 8/2000 | Cowsert | 435/375 |
| 6,107,297 A | 8/2000 | Kindon et al. | 514/252.02 |
| 6,200,981 B1 | 3/2001 | Kindon et al. | 514/269 |
| 6,264,975 B1 | 7/2001 | Boucher, Jr. | 424/434 |
| 6,277,855 B1 | 8/2001 | Yerxa | 514/256 |
| 6,331,529 B1 | 12/2001 | Yerxa et al. | 514/47 |
| 6,436,910 B1 | 8/2002 | Yerxa et al. | 514/47 |
| 6,444,115 B1 | 9/2002 | Hodges et al. | 205/792 |
| 6,462,028 B2 | 10/2002 | Pendergast et al. | 514/47 |
| 6,475,360 B1 | 11/2002 | Hodges et al. | 204/403.14 |
| 6,713,458 B1 * | 3/2004 | Yerxa et al. | 514/47 |
| 2001/0044431 A1 | 11/2001 | Rodriguez | 514/179 |

OTHER PUBLICATIONS

Mason et al, "Changes in the Vaginal Epithelium of the Rat After Vitamin A Deficiency", Journal of Nutrition (1935), 9, 735-755.*
Bouchie, Julie L., "P2Y Receptor Regulation of PAI-1 Expression in Vascular Smooth Muscle Cells", *Arteriosclerosis, Thrombosis, and Vascular Biology*, (Mar. 2000), 866-873.
Garrad, Richard C., "Structural Basis of Agonist-induced Desensitization and Sequestration of the P2Y2 Nucleotide Receptor", *The Journal of Biological Chemistry*, 273 (45), (Nov. 1998), 29437-29444.
Gorodeski, George I., "Expression, Regalation, and Function of P2X4 Purinergic Receptor in Human Cervical Epithelial Cells", *American Journal of Physiology-Cell Physiology*, 282, (2002), C84-C93.
Gorodeski, George I., "Regulation by Retinoids of P2Y2 Nucleotide Receptor mRNA in Human Uterine Cervical Cells", *American Journal of Physiology*, 275, (1998), C758-C765.

(Continued)

*Primary Examiner*—Carlos A. Azpuru
(74) *Attorney, Agent, or Firm*—Schwegman, Lundberg, Woessner, Kluth, P.A.

(57) ABSTRACT

The invention provides compositions and methods for increasing the secretion of mucus within the reproductive tract of a female mammal.

18 Claims, 5 Drawing Sheets

OTHER PUBLICATIONS

Gorodeski, George I., "Regulation of the Paracellular Permeability of Cultured Human Cervical Epithelium by a Nucleotide Receptor", *J. Soc. Gynecol. Invest*, 2 (5), (Sep.-Oct. 1995), 716-720.

Gorodeski, George I., "Regulation of Transcervical Permeability by Two Distinct P2 Purinergic Receptor Mechanisms", *American Journal of Physiology-Cell Physiology*, 282, (2002), C75-C83.

Insel, Paul A., "P2Y Receptors of MDCK Cells: Epithelial Cell Regulation by Extracellular Nucleotodes", *Clinical and Experimental Pharmacology and Physiology*, 28, (2001),351-354.

Jumblatt, James E., "Regulation of Ocular Mucin Secretion by P2Y2 Nucleotide Receptors in Rabbit and Human Conjunctiva", *Experimental Eye Research*, 67, (1998), 341-346.

Santiago-Perez, Laura I., "P2Y2 Nucleotide Receptor Signaling in Human Monocytic Cells: Activation, Desentization, and Coupling ot Mitogen-Activated Protein Kinases", *Journal of Cellular Physiology*, 187, (2001), 196-208.

Velazquez, Betty, "Differential Agonist-induced Desensitization of P2Y2 Nucleotide Receptors by ATP and UTP", *Molecular and Cellular Biochemistry*, 206, (2000), 75-89.

\* cited by examiner

SEQUENCE LISTING

```
<160> NUMBER OF SEQ ID NOS: 10

<210> SEQ ID NO 1
<211> LENGTH: 20
<212> TYPE: DNA
<213> ORGANISM: Homo sapiens

<400> SEQUENCE: 1
tgtcttcgcc ctctgcttcc                                              20

<210> SEQ ID NO 2
<211> LENGTH: 20
<212> TYPE: DNA
<213> ORGANISM: Homo sapiens

<400> SEQUENCE: 2
gtcaggccag gggtgtcatt                                              20

<210> SEQ ID NO 3
<211> LENGTH: 20
<212> TYPE: DNA
<213> ORGANISM: Homo sapiens

<400> SEQUENCE: 3
agtcggttgg agcgagcatc                                              20

<210> SEQ ID NO 4
<211> LENGTH: 20
<212> TYPE: DNA
<213> ORGANISM: Homo sapiens

<400> SEQUENCE: 4
gggcacgaag gctcatcatt                                              20

<210> SEQ ID NO 5
<211> LENGTH: 20
<212> TYPE: DNA
<213> ORGANISM: Homo sapiens

<400> SEQUENCE: 5
ggctgcaagg ccttcttcaa                                              20

<210> SEQ ID NO 6
<211> LENGTH: 20
<212> TYPE: DNA
<213> ORGANISM: Homo sapiens

<400> SEQUENCE: 6
catgcggaac cgagatgatg                                              20
```

```
<210> SEQ ID NO 7
<211> LENGTH: 20
<212> TYPE: DNA
<213> ORGANISM: Homo sapiens

<400> SEQUENCE: 7
cccaaagcac agcaatgtcc                                              20

<210> SEQ ID NO 8
<211> LENGTH: 20
<212> TYPE: DNA
<213> ORGANISM: Homo sapiens

<400> SEQUENCE: 8
agcccaggac tgtggtctgc                                              20

<210> SEQ ID NO 9
<211> LENGTH: 20
<212> TYPE: DNA
<213> ORGANISM: Homo sapiens

<400> SEQUENCE: 9
gctcacgttc agggctgtca                                              20

<210> SEQ ID NO 10
<211> LENGTH: 20
<212> TYPE: DNA
<213> ORGANISM: Homo sapiens

<400> SEQUENCE: 10
gccaccacac catcaccatc                                              20
```

VAGINAL HEALTH PRODUCTS

FIELD OF THE INVENTION

The present invention relates to the use of compounds such as retinoids, carotenoids, nucleotides and nucleosides for moisturizing and improving the health of the female genital tract. Such compounds can increase the secretion of mucus, stimulate cellular growth and gene expression within vaginal and cervical cells and may be useful as contraceptives.

BACKGROUND OF THE INVENTION

Secretory functions of the uterine, cervical and vaginal mucous cells have a profound impact on the function and health of the reproductive tract. For example, the quality and quantity of cervical mucus changes throughout the menstrual cycle and such changes dramatically influence fertility. Under the influence of rising estrogen levels, cervical mucus becomes thin, allowing the passage of spermatozoa. Later in the menstrual cycle, as progesterone levels increase, mucus becomes thick and hostile to sperm penetration, thereby closing the window of fertility. Such thickening of cervical mucus is thought to be one of the primary modes of contraceptive action for progestin-only contraceptives.

Estrogen stimulates the production of thin, isotonic mucus, with increased amounts of high molecular weight glycoproteins. Cervical mucus contains 98% water at mid cycle and 90% water at other times. Cervical mucus is also rich in metallic ions, enzymes (such as alkaline phosphatase, etc.), soluble proteins and salts. The gel phase of cervical mucus contains a high molecular weight glycoprotein called mucin. Mucin forms micelles that cross-link by disulfide bridges. Estrogen and progestogens control the arrangement of these micelles. These micellar arrangements influence the rheological properties of mucus. See Kopito et al. *Water and electrolytes in human cervical mucus*. Fertil. Steril. 1973; 24:499–506; Fordney-Settlage, D. *A review of cervical mucus and sperm interactions in humans*. Int. J. Fertil. 1981; 26:161–169.

As estrogen levels fall in the menopause, estrogen dependent tissue will start to involute and take on the characteristic appearance of estrogen deprivation. Cervical mucus levels diminish and vaginal mucosa regresses during menopause. With aging, the vagina becomes shortened, ruggae disappear, and elasticity is lost. Vaginal secretion becomes scanty. When estrogen is provided, some of these effects are reversed: the cervix may secrete more mucus and the vaginal mucosa may regain lost layers. However, the symptoms often do not disappear completely, in part because the amount of estrogen provided for hormone replacement is lower than circulating estrogen levels during a normal menstrual cycle.

Approximately 40% of postmenopausal women experience atrophic vaginitis or vaginal dryness. During vaginal atrophy, the vaginal epithelium decreases in thickness, hydration, rugae (folds), and blood flow. Causes of atrophic vaginitis include a decrease in the amount of estrogen present both locally and systemically as well as environmental factors such as chemotherapy, antihistamines, smoking cigarettes, excessive exercise, and perineal products (i.e. douches, deodorants, and perfumes). Estrogens or hormone replacement therapies (HRTs) are effective in reducing vaginal dryness. However, possible dangerous side effects include a higher incidence of breast cancer, endometrial cancer, blood clots, nausea, breast tenderness, and headache. Products that are available over-the-counter include lubricants such as Astroglide and KY Lubricating Jelly as well as moisturizers such as Replens and KY Long Lasting Moisturizer. These products, which are mostly water in composition, provide only temporary relief (1–2 days) for symptoms and provide virtually no long-term benefits to the vaginal tissue.

Therefore, vaginal dryness and lack of lubrication is a problem, particularly after menopause. Stimulation of cervical mucus production can help alleviate vaginal dryness, and can also augment the action of exogenously administered estrogen to alleviate vaginal dryness. Accordingly, compositions and methods for modulating mucus levels in the human vagina are needed.

SUMMARY OF THE INVENTION

The invention provides non-hormonal therapies for treating certain reproductive and vaginal problems, including atrophic vaginitis. In general, these therapies have minimal side effects, stimulate natural and non-hormonal mechanisms of action, increase mucus secretion, stimulate gene expression, replace aging tissues with new tissues and maintain or restore healthy tissue function.

Thus, the present invention is directed to a variety of methods of treating or preventing vaginal and/or reproductive problems in a female mammal. These methods involve administering to the female mammal an effective amount of retenoid or carotenoid and/or one or more nucleotide(s) or nucleoside(s). In general, administration is topical or intravaginal. These methods can inter alia modulate mucus levels to enhance or diminish fertility in a female mammal, or to alleviate or diminish vaginal dryness in a female mammal.

In one embodiment, the invention provides a method to increase growth of vaginal or cervical epithelial cells by administering to the female mammal an effective amount of retenoid or carotenoid and/or one or more nucleotide(s) or nucleoside(s).

In another embodiment, the method involves increasing the expression of $P2Y_2$ receptors or estrogen receptors or vascular endothelial growth factor in vaginal or cervical epithelial cells by administering to the female mammal an effective amount of retenoid or carotenoid and/or one or more nucleotide(s) or nucleoside(s).

In yet another embodiment, the invention provides a method to increase expression of mucin, for example, mucin-4, in vaginal or cervical epithelial cells by administering to the female mammal an effective amount of retenoid or carotenoid and/or one or more nucleotide(s) or nucleoside(s). Such methods can prevent or treat vaginal dryness in a mammal, or maintain or enhance the normal protective function of vaginal mucus in a mammal. In general, the retenoid, carotenoid, nucleotides or nucleosides and other compounds are administered intravaginally.

One or more nucleotide(s) or nucleoside(s) may also be administered in a composition that contains vitamin A and/or related compound(s). Such nucleotide(s) or nucleoside(s) include, for example, dATP, dGTP, dCTP, dTTP, dUTP, ATP, GTP, CTP, TTP, UTP, and any derivative of such nucleotide(s) or nucleoside(s) that is available to one of skill in the art.

DESCRIPTION OF THE FIGURES

FIG. 1 illustrates the effects of three lower concentrations of trans-retinoic acid (diamond symbols), 9-cis-retinoic acid (square symbols), and 13-cis-retinoic acid (white triangles) on ME-180 cell growth over a period of three days. As a negative control, the effect of adding media without retinoic acid (white crosses) on cell growth is also illustrated.

FIG. 2 illustrates the effects of three higher concentrations of trans-retinoic acid (circles), 9-cis-retinoic acid (square symbols), and 13-cis-retinoic acid (diamonds) on ME-180 cell growth over a period of two days. As a negative control, the effect of media without retinoic acid (crosses) on cell growth is also illustrated.

DETAILED DESCRIPTION OF THE INVENTION

Figure 1A:
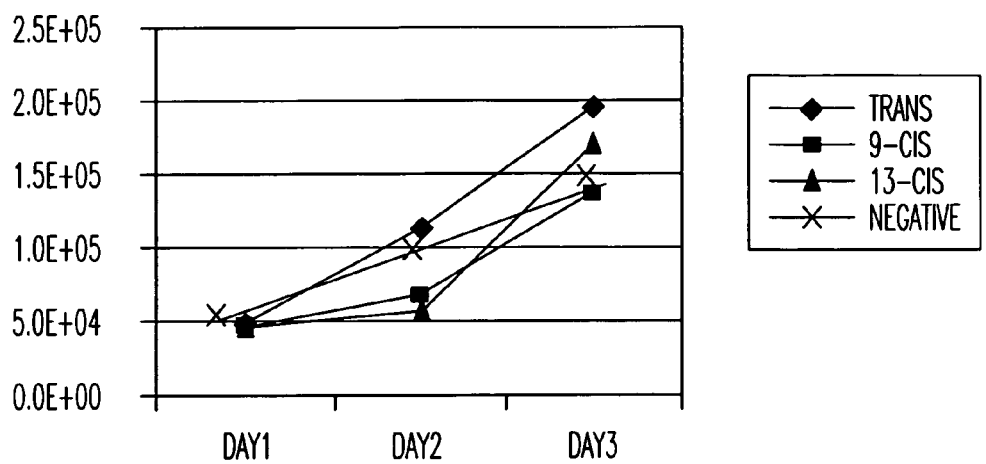
FIG. 1a graphically illustrates the effects of 1 nM of trans-retinoic acid (diamond symbols), 9-cis-retinoic acid (square symbols), and 13-cis-retinoic acid (white triangles) on ME-180 cell growth over a period of three days.

The invention provides methods for increasing the secretion of mucus, increasing the expression of key genes and for stimulating cellular growth within the reproductive system of a female mammal by administering a composition comprising a retenoid or carotenoid (e.g. vitamin A or trans-retinoic acid) to the mammal. The composition can also include one or more deoxynucleotide(s) or nucleoside(s). Such administration can increase the expression and activation of key genes like receptors, growth factors and other genes within vaginal and cervical epithelial cells. Administration of the compositions of the invention can also stimulate cellular growth of vaginal and cervical cells, thereby replacing older cells and rejuvenating the lining of the female reproductive tract.

This invention utilizes inexpensive, readily available active compounds that are already used by the body and that simply and effectively enhance the natural ability of the vaginal and cervical tissue to renew itself and to produce moisture. The cell types, gene products and moisture produced by the methods of the invention are of the type that are naturally found in the vagina or cervix. The methods and compositions of the invention therefore avoid strong chemicals and unnatural substances whose effects on the health and reproduction of the user are unknown.

The methods of the invention may change the quantity and quality of the secretions of the reproductive organs, repair and replace aging tissues and influence expression of genes within reproductive, epithelial and mucosal cells. Genes whose expression may be influenced by the methods of the invention include mucin genes, receptor genes, growth factor genes, protein kinase genes, and the like.

Mucins refer to a family of glycoproteins of high molecular weight, secreted or expressed by goblet and nongoblet epithelial cells of mucosal tissues. Mucins can form mucus, a highly hydrated gel of particular structure and function. Mucins from diverse species have similar structural features, particularly with regard to the mucin protein backbone. Nine distinct mucin genes have been identified (MUC1, 2, 3, 4, MUC5AC, MUC5B, MUC6, 7 and 8). Mucins are glycoproteins containing from fifty to eighty percent carbohydrate. They are large, elongated molecules (molecular weight $10^5$ to $10^7$ daltons) with a protein backbone to which oligosaccharides are attached in a bottle-brush configuration. The oligosaccharide side chains, or bristles, can be highly variable in their make-up, indicating that the more basic functions of the molecule derive from the protein core.

These molecules can be crosslinked through disulfide bridges to form very high molecular weight gels. Different tissues may produce different types of mucins.

According to the invention, retenoids and carotenoids (e.g. vitamin A) can increase the expression of mucins and thereby provide increased secretion and formation of mucus within the reproductive tracts of female mammals.

The expression of receptors such as the $P2Y_2$ receptor, the estrogen receptor alpha (ER-$\alpha$), and the like is also increased by use of the methods of the invention. For example, increased expression and activation of $P2Y_2$ receptor provides a greater opportunity for dNTPs to bind to this receptor on epithelial cells, which results in the secretion of mucin from the cell. Similarly, increased expression and activation of the estrogen receptor alpha provides a greater opportunity for estrogen to bind estrogen and activate the cascade of biochemical events regulated by this receptor.

Moreover, the expression of growth factor genes can be increased by activating the $P2Y_2$ receptor through the methods of the invention. Such growth factor genes include, for example, vascular endothelial growth factor (VEGF), epidermal derived growth factor, platelet derived growth factor, and other growth factors.

The expression of kinases, and of proteins whose activity is modulated by phosphorylation, can also be regulated by activating the $P2Y_2$ receptor using the methods of the invention. For example, activation of the $P2Y_2$ receptor leads in a rather direct manner to the expression of soluble guanylyl cyclase (GC-S) and cGMP-dependent protein kinase (PKG). The activity and function of proteins phosphorylated or de-phosphorylated by such kinases or cyclases can also be influenced by the expression levels of these kinases or cyclases. Activation of the $P2Y_2$ receptor can initiate a cascade of events leading to increased kinase and/or phosphatase levels and changes in the amount of phorphorylation in proteins that interact with such kinases and/or phosphatases. For example, protein phosphatase 2A (PP2A) dephosphorylates a myristoylated alanine-rich C kinase substrate (MARCKS) protein that is involved in the secretion of mucin. The activities of MARCKS and similar proteins can be modulated by changing the level of phosphorylation on these proteins. Hence, the activation of the $P2Y_2$ receptor may modulate the expression and/or activity of proteins such as soluble guanylyl cyclase (GC-S), cGMP-dependent protein kinase (PKG), protein kinase C (PKC), protein phosphatase 2A (PP2A) and the MARCKS protein. The effect of activating the $P2Y_2$ receptor and other genes is to increase secretion of mucus in the reproductive system of a female mammal.

Influences on mucus secretion that may be provided by the invention include, but not limited to, the quantity and type of mucin (e.g. sulfo and/or sialomucin), changes in viscosity, hydrogen ion retardation, hydrophobicity, changes in phospholipid content, glycosylation and sulfation, macromolecular assembly, surface tension, adhesivity, transport properties, elastic modulus, tensile properties, rigidity factors, recoil factors, spinnbarkeit, sperm penetration qualities, consistency, cellularity, ferning, and the like.

The methods of the invention can change the constitutive and stimulated secretions of the local reproductive system, including those of the vagina, cervix, uterus, fallopian tube, Bartholin or vestibular glands and urethral secretions. The methods and compositions of the invention can influence the function of the mucus genes found in the reproductive system, including, but not limited to genes that control mucus production in the cervix, uterus, and Bartholin's glands and other parts of the reproductive system with mucus secreting cells. The squamous epithelium of the lower genital tract (vagina; for example) and epithelial cells of the cervix can be treated by the methods of the invention. Included are methods to influence or change the secretary effects of the mucus genes, mucus secreting cells and cells that influence the properties of secretory and cell surface mucins of all the above mentioned glands of the reproductive system.

Mucus can be defined by its chemical, physical and biological properties. Rheological or flow properties of mucus include viscosity, rate of flow, shear index, spinnbarkeit or stretch of mucus due to increased viscoelasticity and ferning (crystallization) parameters. Changing or stimulating the hydration, viscosity, quantity or other properties of vaginal secretions can influence a variety of conditions and disorders, including, but not limited to contraception, infertility, menopause, dyspareunia, infections, and others related and unrelated conditions. Description of the function and anatomy of these organs can be found in Novak's Gynecology, 12.sup.th edition, eds. Berek, Adashi and Hillard, Williams and Wilkins, Baltimore, Md., 1996.

The methods and compositions of the invention can also increase the growth of cells lining the female reproductive tract, for example, vaginal and cervical cells. Such increased cell growth may occur very quickly, or after only a few days of treatment. For example, after only two to three days of treatment the number of newly formed cells can be twice or three times or four times or five times that of untreated individuals. As treatment progresses the number of newly formed cells can increase further. For example, treated individuals may have about 2 to about 20 times the number of young, newly formed cells compared to untreated individuals. Other individuals may have about 2 to about 10 times the number of young, newly formed cells as untreated individuals. Such increased cell growth can repair and replace aging cells and tissue, rejuvenate the lining of the female reproductive tract and provide greater resilience and improved health to tissues involved in reproduction.

The invention therefore has at least two general utilities. First, the invention may increase the amount of mucus and/or the water content of secretions of the reproductive organs to improve the health and to increase lubrication of the female reproductive system. Such an increased amount of mucus may also inhibit reproduction or provide contraception. Second, the invention may be used to rejuvenate aging tissues and enhance the health and resiliency of those tissues, for example, by stimulating cellular growth, gene expression and mucus secretion.

Female Reproductive System

As an active gatekeeper to the internal reproductive organs, the uterine cervix plays a critical role in reproduction. The following functions can be attributed to vaginal/cervical mucus and its role in reproduction: 1) Semen is filtered at the cervical os and sperm allowed entry into the uterus from a relatively hostile vaginal environment; 2) Sperm are nurtured within the cervical canal and supported and prepared for capacitation; 3) Sperm are stored and later released in order to co-ordinate with ovulation. Katz, D. F. Human Cervical Mucous: Research Update. Am. J. Obstet. Gynecol. 1991:165:1984–6.

Under the influence of estrogen, cervical mucus becomes thin and less viscous, with a ferning pattern seen when spread on a slide. Katz, D. F. Human Cervical Mucous: Research Update. Am. J. Obstet. Gynecol. 1991:165:1984–6. The actual mechanism whereby estrogen changes the cervical mucus is not clearly understood. But see, Nicosia S V. Physiology of the Cervical Mucus. Sem. In Reproductive Endocrinology. 1986;4:313–321. Cervical mucus is a mixture of mucin secreted by the mucus cells and transudation of capillary exudates, which include water (85–98%), electrolytes, serum and locally derived proteins. The mucins are responsible for the rheological properties of mucus, but comprise less than 1% in volume. Apparently, during the mid-cycle, estrogens stimulate the stromal cells, which in turn stimulate the mucus cells. The mucus produced during this time has a higher water content, accounting for part of the rheological changes such as ferning.

Under the influence of estrogen, the human cervix secretes a profuse, clear and thin mucus, at a rate of about 600 mg of mucus a day, in the pre-ovulatory and ovulatory phases of the menstrual cycle. Under the influence of progestins, this rate decreases to 20–60 mg/day and the mucus is thick and viscous. Moghissi, K S. The function of the cervix infertility. Fert. Steril. 1972 23:295–306.

The viscosity of cervical mucus changes in a parallel fashion with externally administered progestins given as contraceptive products. For example, Norplant, a levonorgestrel containing implant, changes cervical mucus within 3 days of insertion and this action is considered one of the critical factors responsible for its contraceptive action. Dunson T R et al. Timing on onset of contraceptive effectiveness in Norplant implant users. Part I. Changes in cervical mucus. Fert. Steril. 1998;69:258–66. A similar finding was shown with another progestin only product—Depo-Provera. Petta C A et al. Timing of onset of contraceptive effectiveness in Depo-Provera users: Part I. Changes in cervical mucus. Fertil Steril. 1998;69:252–7. Clearly, changes in cervical mucus could have a contraceptive effect because the secretion of progesterone is associated with a considerable decrease in fecundity and a closing of the window of fertility.

The P2Y$_2$ Pathway

P2Y$_2$ receptors are P2-purinoceptors are transmembrane receptors on epithelial cells that interact with purines, particularly with ATP and UTP. P2-purinoceptors comprise two major families, P2X and P2Y. Each family consists of at least seven members ($X_{1-7}$ and $Y_{1-7}$). The P2X family represents cell membrane ligand-binding ion channels permeable to Na$^+$, K$^+$, and Ca$^{++}$. The P2Y-purinoceptors constitute G-protein-linked receptors, often coupled to phospholipase C and, hence, to inositol triphosphate formation. There are at least seven different subclasses of P2Y receptor, based upon agonist potency profiles. For a description of the various P2Y subtypes, see, for example, Abbrachio and Burnstock, Pharmac. Ther. 64, 445–475, 1994, the entire disclosure of which is incorporated herein by reference.

The P2Y$_2$ pathway can be manipulated by the methods of the invention. This pathway begins with the binding of nucleotide(s) or nucleoside(s) to the P2Y$_2$ receptor that is on or within the epithelial cell membrane. This pathway is typically linked to the activation of protein kinase C (PKC). Activation of protein kinase C leads to increased levels of inositol 1,4,5-triphosphate and diacylglycerol, resulting in the influx of Ca$^{2+}$ (Garrad et al., J. Biol. Chem. 1998, 273(45), 29437–29444). Protein kinaseC activation has also been shown to affect mucin secretion (Li et al., J. Biol. Chem. 2001, 276 (44):40982–90). Activated protein kinase C may phosphorylate a protein called myristoylated alanine-rich C kinase substrate (MARCKS) that then migrates from the plasma membrane into the cytoplasm of epithelial cells. The phosphorylated-MARCKS protein is dephosphorylated by protein phosphatase 2A (PP2A) in the cytoplasm, and thereby regains its capacity to bind membranes. MARCKS may associate with actin and myosin and may thereby mediate the movement of mucin-containing granules to the cell periphery. Hence, a series of biochemical events take place after dNTP-P2Y$_2$ receptor binding that eventually results in the secretion of mucin, a glycoprotein that is a component of mucus. Mucin causes a natural lubricating and moisturizing effect in the female genital tract.

According to the invention, vitamin A (retinoic acid) increases expression of the P2Y$_2$ receptor and also increases cellular proliferation of vaginal and cervical epithelial cells.

Retinoids and Carotenoids

The compositions of the invention can include one or more retinoids or carotenoids. The IUPAC-IUB Joint Commission on Biochemical Nomenclature states that "retinoids are a class of compounds consisting of four isoprenoid units joined in a head to tail manner. All retinoids may be formally derived from a monocyclic parent compound containing five carbon-carbon double bonds and a functional group at the terminus of the acyclic portion. The basic retinoid structure can be subdivided into three segments, namely the polar terminal end, the conjugated side chain, and the cyclohexenyl ring. The basic structures of the most common natural retinoids are called retinol, retinaldehyde, and retinoic acid. However, retinoids of this invention are not limited to just retinol, retinaldehyde, and retinoic acid. Instead, the retinoids and carotenoids of the invention also include compounds falling within Formula IA or IB:

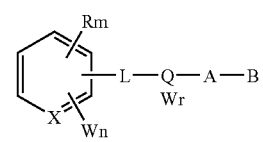

IA

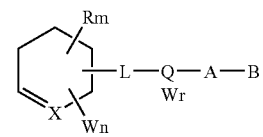

IB wherein:
X is CH, or N;
R is H or alkyl of 1 to 6 carbons;
m is an integer having the value of 0–5;
n is an integer having the value of 0–2;
r is an integer having the value 0–2;
L is —(C=Z)—NH— or —NH—(C=Z)— where Z is O or S;
Q is a phenyl, naphthyl, pyridyl, thienyl, furyl, pyridazinyl, pyrimidinyl, pyrazinyl, thiazolyl, oxazolyl, imidazolyl or pyrrazolyl, wherein the phenyl, naphthyl pyridyl, thienyl, furyl, pyridazinyl, pyrimidinyl, pyrazinyl, thiazolyl, oxazolyl, imidazolyl or pyrrazolyl group can be substituted with one or two R$^1$ groups;
W is F, Br, Cl, I, C$_{1-6}$alkyl, fluoro-substituted C$_{1-6}$alkyl, NO$_2$, N$_3$, OH, OCH$_2$OCH$_3$, OC$_{1-10}$alkyl, tetrazol, CN, SO$_2$C$_{1-6}$-alkyl, SO$_2$C$_{1-6}$-fluoro-substituted alkyl, SO—C$_{1-6}$ alkyl, CO—C$_{1-6}$alkyl, COOR$_8$, phenyl, phenyl itself substituted with a W group other than with phenyl or substituted phenyl, with the proviso that when X is CH and r is 0 then n is not 0 and at least one W group is not alkyl;
A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; and B is COOH or a pharmaceutically acceptable salt thereof, COOR$^8$, CONR$^9$R$^{10}$, CH$_2$OH, CH$_2$OR$^{11}$, CH$_2$OCOR$^{11}$, CHO, CH(OR$^{12}$)$_2$, CHOR$^{13}$O, COR$^7$, CR$^7$(OR$^{12}$)$_2$, CR$^7$OR$^{13}$O, where R$^7$ is an alkyl, cycloalkyl or alkenyl group containing 1 to 5 carbons, R$^8$ is an alkyl group of 1 to 10 carbons or trimethylsilylalkyl where the alkyl group has 1 to 10 carbons, or a cycloalkyl group of 5 to 10 carbons, or R$^8$ is phenyl or lower alkylphenyl, R$^9$ and R$^{10}$ independently are hydrogen, an alkyl group of 1 to 10 carbons, or a cycloalkyl group of 5–10 carbons, or phenyl or lower alkylphenyl, R$^{11}$ is lower alkyl, cycloalkyl, lower alkyl substituted cycloalkyl, phenyl or lower alkylphenyl, R$^{12}$ is lower alkyl, and R$^{13}$ is divalent alkyl radical of 2–5 carbons.

In some embodiments, the retinoid or carotenoid is a compound defined by Formula II:

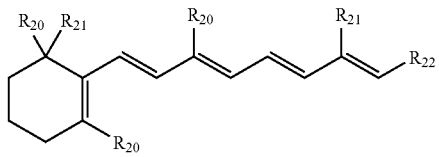

wherein:

R$_{20}$, R$_{21}$ and R$_{22}$ are each independently C$_{1-6}$ alkyl, fluoro-substituted C$_{1-6}$ alkyl, hydroxy-substituted C$_{1-6}$ alkyl, CH$_2$OH, CH$_2$OR$^{11}$, CH$_2$OCOR$^{11}$, CHO, CH(OR$^{12}$)$_2$, CHOR$^{13}$O, COR$^7$, CR$^7$(OR$^{12}$)$_2$, or CR$^7$OR$^{13}$O.

The term alkyl refers to and covers any and all groups that are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means alkyl groups having 1 to 6 carbons, and 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

Compounds of Formula IA, IB and II can be made as described in U.S. Pat. Nos. 6,437,129 and 6,437,003, which are incorporated herein in their entirety.

A pharmaceutically acceptable salt may be prepared for any compounds in this invention having a functionality capable of forming such a salt, for example, an acid or amine functionality. A pharmaceutically acceptable salt is any salt that retains the activity of the parent compound and does not impart any deleterious or untoward effect on the subject to which it is administered and in the context in which it is administered. Pharmaceutically acceptable salts may be derived from organic or inorganic bases. The salt may be a mono or polyvalent ion. Of particular interest are the inorganic ions, sodium, potassium, calcium, and magnesium. Organic salts may by be made with amines, particularly ammonium salts such as mono-, di- and trialkyl amines or ethanolamines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide.

Preferred salts are those formed with inorganic acids such as hydrochloric acid, sulfuric acid or phosphoric acid. Any of a number of simple organic acids such as mono-, di- or tri-acid may also be used.

Some of the compounds of the present invention may have trans and cis isomers. In addition, the compounds of the present invention may contain one or more chiral centers and therefore may exist in enantiomeric and diastereomeric forms. The scope of the present invention is intended to cover all such isomers, as well as mixtures of cis and trans isomers, mixtures of diastereomers and racemic mixtures of enantiomers (optical isomers) as well.

Nucleosides and Nucleotides

The compositions of the invention can include one or more nucleosides or nucleotides. Such nucleotide or nucleosides can include, for example, dATP, dGTP, dCTP, dTTP, dUTP, ATP, GTP, CTP, TTP, UTP, and any derivative of such nucleotide(s) or nucleoside(s) that is available to one of skill in the art.

In some embodiments, the nucleotide or nucleoside is a compound defined by Formula III:

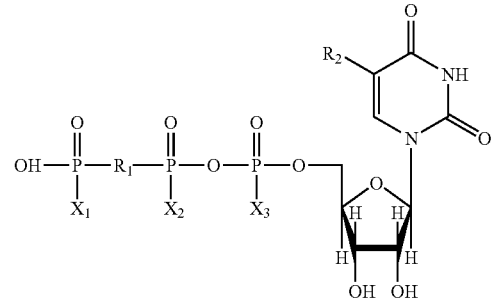

wherein:

X$_1$, X$_2$ and X$_3$ are each independently either O$^-$ or S$^-$. In some embodiments, X$_2$ and X$_3$ are each O$^-$;

R$_1$ is O, imido, methylene, or dihalomethylene (e.g., dichloromethylene, diflouromethylene). Preferably, R$_1$ is oxygen or difluoromethylene.

R$_2$ is H or Br. Preferably, R$_2$ is H. Examples of compounds of Formula III are uridine 5'-triphosphate (UTP) and uridine 5'-O-(3-thiotriphosphate) (UTPγS).

In other embodiments, the nucleotide or nucleoside is a compound defined by Formula IV:

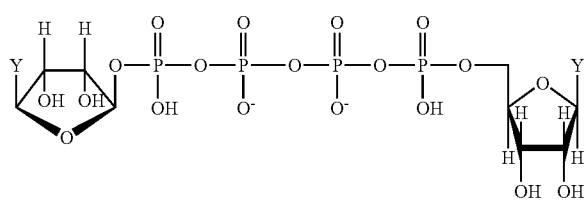

wherein Y is uracil or adenine.

In further embodiments, the nucleotide or nucleoside is a compound defined by Formula V:

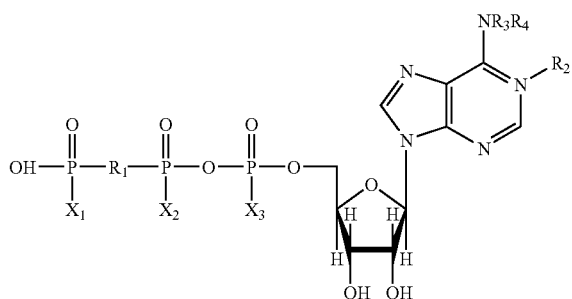

wherein:

$X_1$, $X_2$, $X_3$ and $R_1$ are as defined above;

$R_3$ and $R_4$ are H when $R_2$ is nothing and there is a double bond between N-1 and C-6 (adenine), or $R_3$ and $R_4$ are H when $R_2$ is O and there is a double bond between N-1 and C-6 (adenine 1-oxide), or $R_3$, $R_4$ and $R_2$ taken together are —CH═CH—, forming a ring from N-6 to N-1 with a double bond between N-6 and C-6 (1,$N^6$-ethenoadenine).

In still further embodiments of the invention, the nucleotide or nucleoside is a compound defined by Formula VI:

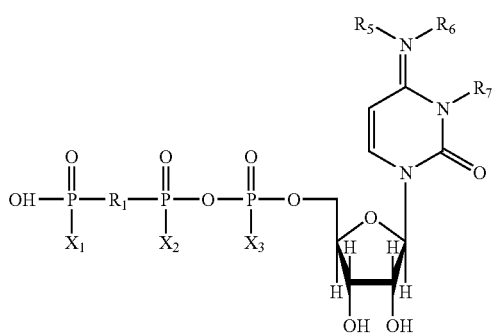

wherein:

$X_1$, $X_2$, $X_3$ and $R_1$ are as defined above;

$R_5$ and $R_6$ are H when $R_7$ is nothing and there is a double bond between N-3 and C-4 (cytosine), or, $R_5$, $R_6$ and $R_7$ taken together are —CH═CH—, and form a ring from N-3 to the nitrogen attached to $R_5$ and $R_6$ (3,$N^4$-ethenocytosine).

Hence, compositions of the invention can contain one or more compounds of Formula III, IV, V or VI in an amount effective to stimulate mucous secretions in the vagina or reproductive passages of a female.

Compounds illustrative of the compounds of Formula III above include: (a) uridine 5'-triphosphate (UTP); (b) uridine 5'—O—(3-thiotriphosphate) (UTPγS); and (c) 5-bromo-uridine 5'-triphosphate (5-BrUTP). These compounds are known or may be made in accordance with known procedures, or variations thereof which will be apparent to those skilled in the art. See generally N. Cusack and S. Hourani, Annals N.Y. Acad. Sci. 603, 172–81 (entitled "Biological Actions of Extracellular ATP"). For example, UTP may be made in the manner described in Kenner, et al., J. Chem. Soc. 1954, 2288; or Hall and Khorana, J. Am. Chem. Soc. 76, 5056 (1954). See Merck Index, Monograph No. 9795 (11th Ed. 1989). UTPγS may be made in the manner described in R. S. Goody and F. Eckstein, J. Am. Chem. Soc. 93, 6252 (1971).

Compounds illustrative of the compounds of Formula IV include $P^1$, $P^4$-di(adenosine-5') tetraphosphate or $P^1$, $P^4$-di(uridine-5') tetraphosphate. These compounds can be made in accordance with known procedures, or variations thereof which will be described by: P. Zamecnik, et al., Proc. Natl. Acad. Sci. USA 89, 838–42 (1981); and K. Ng and L. E. Orgel, Nucleic Acids Res. 15 (8), 3572–80 (1987). $P^1$, $P^4$-di(uridine-5') tetraphosphate can be prepared by methods similar to that described in C. Vallejo, et al., Biochem. Biophys. Acta 438, 304–09 (1976).

Compounds illustrative of the compounds of Formula V above include (a) adenosine 5'-triphosphate (ATP) and (b) 1,$N^6$-ethenoadenosine 5'-triphosphate. Compounds illustrative of the compounds of Formula IV above include (a) cytidine 5'-triphosphate and (b) 3,$N^4$-ethenocytidine 5'-triphosphate. These compounds can be made in accordance with known procedures, or variations thereof which will be apparent to those skilled in the art. For example, phosphorylation of nucleosides by standard methods such as D. Hoard and D. Ott, J. Am. Chem. Soc. 87, 1785–1788 (1965); M. Yoshikawa, et al., Tetrahedron Lett. 5065–68 (1967) and idem., Bull. Chem. Soc. (Jpn) 42, 3505–08 (1969); J. Moffatt and H. Khorana, J. Am. Chem. Soc. 83, 649–59 (1961); and B. Fischer, et al., J. Med. Chem. 36, 3937–46 (1993) and references therein. Etheno derivatives of cytidine and adenosine are prepared by known methods such as: N. Kotchetkov, et al., Tetrahedron Lett. 1993 (1971); J. Barrio, et al., Biochem. Biophys. Res. Commun. 46, 597 (1972); J. Secrist, et al., Biochemistry 11, 3499 (1972); J. Bierndt, et al., Nucleic Acids Res. 5, 789 (1978); K. Koyasuga-Mikado, et al., Chem. Pharm. Bull. (Tokyo) 28, 932 (1980). Derivatives with alpha, beta and gamma thiophosphorus groups can be derived by the following or by adapting methods of: J. Ludwig and F. Eckstein, J. Org. Chem. 54, 631–35 (1989); F. Eckstein and R. Goody, Biochemistry 15, 1685 (1976); R. Goody and F. Eckstein, J. Am. Chem. Soc. 93, 6252 (1971).

Compounds of Formulas III, V or VI where $R_1$ is $CCl_2$ and $CF_2$ can be prepared by methods similar to that described in G. Blackburn, et al., J. Chem. Soc. Perkin Trans. I, 1119–25 (1984). Compounds of Formula I, II, III where $R_1$ is $CH_2$ can be prepared by methods similar to that described in T. Myers, et al., J. Am. Chem. Soc. 85, 3292–95 (1963).

In addition, UTP, ATP, CTP, $P^1P^4$-di(adenosine-5') tetraphosphate, 3,$N^4$-ethenocytidine triphosphate, 1,$N^6$-ethenoadenine 5'-triphosphate, adenosine 1-oxide 5'-triphosphate, ATPγS, ATPβS, ATPαS, AMPPCH$_2$—P, AMPPNHP, $N^4$-ethenocytidine and 1,$N^6$-ethenoadenosine are commercially available, for example, from Sigma Chemical Company, PO Box 14508, St. Louis, Mo. 63178.

METHODS OF USE

The present invention is directed to a variety of methods of treating or preventing vaginal and/or reproductive problems in a female mammal. These methods involve administering to the female mammal an effective amount of retinoid or carotenoid and/or one or more nucleotide(s) or nucleoside(s). In general, administration is topical or intravaginal.

Treatment of, or treating, vaginal and/or reproductive problems in a female mammal is intended to include modulation of mucus levels to enhance or diminish fertility in a female mammal, or to alleviate or diminish vaginal dryness in a female mammal. The treatment therefore can include alleviation or diminishment of more than one vaginal and/or reproductive problem in a female mammal.

In one embodiment, the method increases growth of vaginal or cervical epithelial cells. In another embodiment, the method involves increasing the expression of $P2Y_2$ receptors or estrogen receptors or vascular endothelial growth factor in vaginal or cervical epithelial cells. Such methods can prevent or treat vaginal dryness in a mammal, or maintain or enhance the normal protective function of vaginal mucus in a mammal.

The term "mammal," as used herein, refers to an animal, in general, a warm-blooded animal. Mammals include cattle, buffalo, sheep, goats, pigs, horses, dogs, cats, rats, rabbits, mice, and humans. Also included are other livestock, domesticated animals and captive animals.

Treatment involves administering an effective amount of retinoid or carotenoid, vitamin A, a vitamin A precursor or a related retinoic acid, retinal or retinol compound to a female mammal. A vitamin A precursor is a compound that can give rise to vitamin A, for example, carotenoid such as beta-carotene. A related retinoic acid, retinal or retinol compound has activity similar to vitamin A. The retinoids, vitamin A, vitamin A precursors and/or related compound(s) may be administered as a composition that contains other ingredients, for example, one or more nucleotide(s) or nucleoside(s), other vitamins (e.g., vitamin E), aloe vera and the like. In general, compositions containing vitamin A and other compound(s) are administered intravaginally.

Compositions

The compositions of the invention are administered to improve the health of the female reproductive system, to stimulate secretion of lubricating fluids and/or to inhibit reproduction.

To achieve the desired effect(s), the composition may be administered as single or divided dosages, for example, of at least about 0.001 µg/kg to about 100 to 200 mg/kg, of about 0.01 µg/kg to about 30 to 50 mg/kg, about 0.1 µg/kg to about 10 to 20 mg/kg or about 1.0 µg/kg to about 1.0 to about 10 mg/kg of body weight of one or more retinoid or carotenoid or nucleotide or nucleoside, although other dosages may provide beneficial results. The amount administered will vary depending on various factors including, but not limited to, the disease, the weight, the physical condition, the health, the age of the mammal, and whether prevention of reproduction or treatment of vaginal dryness is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions of the invention may be essentially continuous over a pre-selected period of time or may be in a series of spaced doses. Local administration is generally contemplated.

The compositions are prepared by combining the active ingredients in the appropriate concentrations. Other active or inactive agents selected by one of skill in the art can optionally be added. The absolute weight of a given active agent included in a unit dose can vary widely. For example, about 0.001 µg to about 50 mg, or about 0.01 µg to about 10 mg, or about 0.1 µg to about 1 mg, of at least one retinoic acid derivative or deoxynuleotide triphosphate, or of a plurality of retinoids or carotenoids and nucleotides or nucleosides can be administered. Alternatively, the unit dosage can vary from about 0.001 µg to about 1000 µg, from about 0.01 µg to about 750 µg, from about 0.1 µg to about 1 mg, from about 1.0 µg to about 750 µg, from about 2.5 µg to about 600 µg, from about 5.0 µg to about 500 µg, or from about 7.5 µg to about 400 µg.

Daily doses of the compositions of the invention can vary as well. Such daily doses can range, for example, from about 0.001 mg/day to about 50 mg/day, from about 0.01 mg/day to about 25 mg/day, from about 0.1 mg/day to about 12 mg/day, from about 0.1 mg/day to about 8 mg/day, from about 0.1 mg/day to about 4 mg/day, and from about 0.1 mg/day to about 2 mg/day of one or more retinoids or carotenoids or nucleotides or nucleosides.

The concentration of retinoids or carotenoids or nucleotides or nucleosides within a composition can also vary. For example, the concentration can vary from about 1 µM to about 1000 µM, or from about 5 µM to about 500 µM, or from about 7 µM to about 300 µM, or from about 8 µM to about 200 µM, or from about 10 µM to about 100 µM.

Thus, one or more suitable unit dosage forms comprising the therapeutic compositions of the invention can be administered by a variety of routes including oral, parenteral (including subcutaneous, intravenous, intramuscular and intraperitoneal), rectal, dermal, transdermal, intrathoracic, intrapulmonary intravaginal and intranasal (respiratory) routes. The therapeutic compositions may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic compositions of the invention are prepared for intravaginal administration, they are generally combined with a pharmaceutically acceptable carrier, diluent or excipient to form a pharmaceutical formulation, or unit dosage form. For intravaginal administration, the compositions may be present as a solution, a suspension, an emulsion, a powder, a granular formulation, or in a natural or synthetic polymer or resin. The active compositions may also be presented as a bolus or paste. Intra vaginally administered therapeutic compositions of the invention can also be formulated for sustained release, e.g., the compositions can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic compositions of the invention can be prepared by procedures known in the art using well-known and readily available ingredients. For example, the composition can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like. The compositions of the invention can also contain other vitamins such as vitamin B, vitamin C or vitamin E. In one embodiment, the compositions of the invention can also contain aloe vera.

The therapeutic compositions of the invention can also be formulated as emulsions, suspensions, aqueous or anhydrous solutions or dispersions, or alternatively the form of an emulsion or suspension or salve for convenient intravaginal administration. The active compositions and other ingredients may form suspensions, solutions, or emulsions in oily or aqueous vehicles, and may contain formulatory agents such as suspending, stabilizing and/or dispersing agents. Alternatively, the active compositions and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$–$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the compositions are well suited to formulation as sustained release dosage forms and the like. The formulations can be so constituted that they release the active composition within the female reproductive system over a period of time. Coatings, envelopes, and protective matrices may be made, for example, from polymeric substances, such as polylactide-glycolates, liposomes, microemulsions, microparticles, nanoparticles, or waxes.

For intravaginal administration, the therapeutic agents may be formulated as is known in the art for direct application to the vaginal area. Forms chiefly conditioned for vaginal application take the form, for example, of creams, milks, gels, dispersion or microemulsions, lotions thickened to a greater or lesser extent, impregnated pads, ointments, aerosol formulations (e.g., sprays or foams), creams, lotions, pastes, jellies, sprays, and aerosols. Alternatively, the composition can be formulated to be part of an adhesive polymer, such as polyacrylate or acrylate/vinyl acetate copolymer.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. The active compositions can also be delivered via iontophoresis, e.g., as disclosed in U.S. Pat. Nos. 4,140,122; 4,383,529; or 4,051,842. The percent by weight of a therapeutic agent of the invention present in a vaginal formulation will depend on various factors, but generally will be from 0.01% to 95% of the total weight of the formulation, and typically 0.1–85% by weight.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions with a pH of about 4.5 to about 5.5.

Furthermore, the active ingredients may also be used in combination with other therapeutic agents, for example, anti-microbial agents, pain relievers, anti-inflammatory agents, vitamins (e.g., vitamin B, C or E), aloe vera and the like, whether for the conditions described or some other condition.

The present invention further pertains to a packaged pharmaceutical composition for controlling reproduction and/or vaginal dryness such as a kit or other container. The kit or container holds a therapeutically effective amount of a pharmaceutical composition for controlling reproduction and/or vaginal dryness and instructions for using the pharmaceutical composition for control of reproduction and/or vaginal dryness. The pharmaceutical composition includes a composition of the present invention, in a therapeutically effective amount such that vaginal dryness is controlled.

In addition, the invention provides a vaginal insert that can release the retinoids, carotenoids, and/or nucleosides in a controlled fashion. Such a vaginal insert can be biodegradable or non-biodegradable. The vaginal insert provides sustained release of the active ingredients at an appropriate rate for achieving the desired level of mucus secretion, gene expression and cellular proliferation.

In some embodiments, the active ingredients can be formulated with oleaginous bases or ointments to form the vaginal insert. This class of formulations comprises the active ingredients and hydrocarbon-based semisolids containing dissolved and/or suspended bacteriostats/preservatives and a buffer system. The petrolatum component in these bases can be any paraffin ranging in viscosity from mineral oil employing incorporated isobutylene, colloidal silica, or stearate salts to paraffin waxes. White and yellow petrolatum are examples of such systems. Bases of this class can be made by incorporating high-melting waxes into a fluid mineral oil via fusion or by incorporation of polyethylene into mineral oil at elevated temperature. Polysiloxanes (also known as silicones) are suitable for use in these bases and typically have a viscosity in the range of about 0.5 to 10.sup.6 centistokes. The organic entities attached to the polysiloxane are preferably lower molecular weight hydrocarbon moieties having from 1 to 8 carbons each, such as lower alkyl, lower alkenyl, phenyl and alkyl substituted phenyl, and phenyl(lower)alkyl, such as benzyl. In such a moiety, each lower alkyl or alkenyl group preferably has 1 to 3 carbons inclusive, such as in a dimethylsiloxane polymer.

Absorption bases can used with such an oleaginous system. In addition to the active ingredients, additional ingredients with the capacity to emulsify a significant quantity of water are employed. Water-in-oil (w/o) emulsions can be formed wherein the external phase is oleaginous in character. Preservatives/bacteriostats, such as the parabens, buffer systems, etc. can be incorporated into these bases as emulsified aqueous solutions together with the active ingredient. Diverse additives are conveniently used as the emulsifier, and these include, but are not limited to, cholesterol, lanolin (which contains cholesterol and cholesterol esters and other emulsifiers), lanolin derivatives, beeswax, fatty alcohols, wool wax alcohols, low HLB (hydrophobe/lipophobe balance) emulsifiers, and assorted ionic and nonionic surfactants, singularly or in combination.

Water-In-Oil (W/O) emulsion bases can be employed in the vaginal inserts of the invention. These formulations can be an expansion of the general class of absorption bases that includes liquids or creams. They can be prepared by taking a mixture of the active ingredients with oil phase ingredients, bacteriostats/preservatives and buffer salts which are dissolved or suspended therein and to which water has been added to form a water-in-oil emulsion.

Oil-In-Water (O/W) emulsion bases can also be utilized in the vaginal inserts of the invention. These systems are semisolid emulsions, microemulsions, or foam emulsion systems containing metronidazole. Usually such a system has a "creamy white" appearance. Typically, the internal oil phase is in the range in percentage composition of about 10% to about 40% oil by weight and the external phase may contain 80% or more water. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, nonionic or amphoteric surfactants, or with combinations especially of the nonionic surfactants. The examples below are exemplary of these systems, but those skilled in the art will appreciate that substitutions and additions or omissions of the specified components could be made by one who is skilled in the art.

Vaginal inserts and suppositories containing the active ingredients can be, for example, oleaginous in nature that melt at body temperature, or polyethylene glycol-based compositions that dissolve in the vaginal fluids. Additional bases for suppositories are glycerin and glycerinated gelatin.

The active ingredients can also be formulated into vaginal inserts using buffered gels made with gelling agents. Some examples of these gelling agents are: cellulosics, cationic polymers, polyoxyalkylenes, and carboxyvinyl polymers. Cellulosics useful in the formulations of the invention include, for example, methyl cellulose, carboxymethyl cellulose, hydroxyethyl cellulose, and hydroxypropyl cellulose. Cationic Polymers useful in the formulations of the invention include "Polyquaternium-10", a polymeric quaternary ammonium salt of hydroxyethyl cellulose reacted with a trimethyl ammonium-substituted epoxide, and the like. Polyoxyalkylenes useful in the invention include olyoxyethylene-polyoxypropylene esters of lanolin and derivatives thereof. Carboxyvinyl polymers useful for the formulations of the invention include cross-linked acrylic acid polymers, e.g., those commercially available from B. F. Goodrich Co., Akron, Ohio, under the designation CARBOPOL.™.

The vaginal insert can comprise a mixture or coating of polymers that provide release of the active agents at a constant rate over a prolonged period of time. In some embodiments, the vaginal insert comprises water-soluble pore forming agents, such as polyethylene glycol (PEG), that can be mixed with water insoluble polymers to increase the durability of the insert and to prolong the release of the active ingredients. Such a water-soluble pore forming agent can be polyethylene glycol, polypropylene glycol, a mixture or polymer of sugars (lactose, sucrose, dextrose, etc.), salts, poloxamers, polyvinyl alcohol and other water soluble food grade and other excipients.

When PEG is used as a pore forming agent, the molecular weight of PEG is in the range from about 200 to about 20,000, alternatively, from about 400 to about 8,000. For example, PEG having a molecular weight of about 540 to about 8,000 is used. In another embodiment, the PEG has a molecular weight of about or above 1,000 to about 8,000. The molecular weight of PEG used for the coating with the formulation of the invention will depend on the ability of PEG to form a coating film that is non-sticky, having enough strength and creating adequate pore size for controlling the release of active ingredients over the desired time period both in vitro and in vivo.

The pore-forming agent is used in the formulation of the invention in the amount effective to regulate the release of a biologically active compound at a desired rate. Preferably, the effective amount of the pore-forming agent provides long term delivery of the active agent thus increasing the useful life of a sustained-release drug implant. The effective amount of the pore forming agent will depend on the desired rate and duration of the release and the ability to form a continuous microporous film during the coating process. To enable release duration over longer periods of time PEG with higher molecular weights is used. For example, PEG 8000 can provide release over a period of time that is longer than 100 days, when used in a concentration from 10 to 50%, preferably from 20 to 45% and most preferably from 30 to 45%. The concentration of PEG is expressed herein in % weight per dry basis and represents the concentration of PEG in the coating film after drying. Similarly, the thickness of the coating film is from 5 to 50 µm, preferably 30 from 10 to 30 µm and most preferably from 15 to 25 µm.

A good correlation exists between the dissolution rate of active agents and the amount of pore forming agent incorporated in the coating film based on in vitro and in vivo studies shown in the Examples. Depending on the desired length of release, the PEG concentration ranges can be adjusted as needed. For example, in vivo duration of a coated insert may be predicted simply from the in vitro dissolution rate of the active agent at the 120-hour time point.

The vaginal insert of the invention may also comprise a water insoluble polymer. Examples of such polymers are ethylcellulose, acrylic resins, co-polymer of methacrylic acid and acylic acid ethyl ester, polylactic acid, PLGA, polyurethane, polyethylene vinyl acetate copolymer, polystyrene-butadiene copolymer and silicone rubber, or mixtures thereof For example, polymers sold under tradenames Aquacoat ECD 30 and Eudragit RS 30 and NE 30D (registered trademarks of Rhom Tech, Inc.) can be used.

A polymer suitable for use in this invention is a polymer that is capable of forming a continuous coating film during the process of spraying and drying with a pore-forming agent. The rate controlling film prepared with such a polymer is very stable during implantation. The film should have enough strength to withstand tear and inner osmotic pressure, and have the stability not to swell or hydrate during the implantation life.

In one embodiment, the coating formulation of the invention is used to coat pellets comprising the active ingredients that are compressed to form a solid, biodegradable insert and then administered for stimulating mucus secretion, gene expression and/or cellular proliferation.

The invention is further illustrated by the following non-limiting Examples.

EXAMPLE 1

Materials and Methods

Cell Lines. Human cervical epithelial cells (ME-180, ATCC) were propagated in culture at 37° C. in a 5% $CO_2$ atmosphere in McCoy's 5A media (Invitrogen) with 10% heat-inactivated fetal bovine serum (Invitrogen). All trans-, 9-cis-, and 13-cis-retinoic acids were purchased from ICN Biomedicals. Retinoic acid stock solutions were made up in DMSO.

Toxicity & Proliferation Experiments. Cellular toxicity/proliferation experiments were performed by first washing the ME-180 cells with HBSS, and adding 3 mL of trypsin (0.25%) with EDTA to the T75 flask for 15 minutes. ME-180 cells in trypsin were added to 7 mL of McCoy's 5A media with 10% FBS. ME-180 cells were centrifuged for 5 minutes, and the supernatant was removed. ME-180 cells were resuspended in 10 mL of McCoy's 5A media with 10% FBS for counting. ME-180 cells were centrifuged for 5 minutes, and the supernatant was removed. ME-180 cells were resuspended at $6 \times 10^4$ cells per mL (62 mL total volume). One milliliter was added to each of 60 wells in a total of three 24-well plates. ME-180 cells were allowed to adhere to the wells overnight. The media was then removed from the ME-180 cells, and the cells were washed one time with 1 mL of HBSS. One mL of McCoy's 5A media with 10% FBS was added in duplicate on each plate containing the retinoic acids in various concentrations (0–10 μM). ME-180 cells in each plate were counted on day 1, 2, or 3 after the addition of the retinoic acid-containing media.

Cell counting. Media was removed from the ME-180 cells, and the cells were washed one time with 1 mL of HBSS. Trypsin was added (150 μL) to each well for ~15 minutes to remove cells. One mL of McCoy's 5A media with 10% FBS was added to each well. ME-180 cells were mixed thoroughly and counted using a hemocytometer.

RNA Extraction from ME-180 cells. ME-180 cells were plated at $2 \times 10^5$ cells per T25 flask (5 mL total volume) and were allowed to propagate for four days. On day four, the media was removed. Five mL of McCoy's 5A media with 10% FBS containing 0, 10 nM, 100 nM, or 1 μM transretinoic acid were added to ME-180 cells in duplicate. ME-180 cells were incubated with these solutions for 4, 8, 16, or 24 hours. The media was removed, and 700 μL of lysis buffer was added to the flasks. The cells were scraped off of the flask with a cell scraper. The RNA was isolated using the Ambion RNAqueous kit according to the manufacturer's instructions. Precipitated RNA was resuspended in DEPC-treated water with 1 μL of RNase inhibitor. Total cervical RNA used as a control was purchased from Ambion, Inc.

Reverse Transcripton of RNA. Approximately 7 μL of RNA was incubated with 3 μL of primer at 80° C. for 10 minutes then immediately placed on ice. A master mix containing 4 μL DEPC water, 4 μL 5× reaction buffer, 1 μL dNTPs, 1 μL of RNase inhibitor, and 1 μL of reverse transcriptase was made for the reactions. Ten μL of master mix was added to the RNA/primer solution and placed at 42° C. for 2 hours. The resulting cDNA was incubated with 3.5 μL of NaOH solution at 70° C. for 10 minutes to hydrolyze the remaining RNA. Five μL of 0.5M Tris/EDTA was added to neutralize the solution. To precipitate the cDNA, 125 μL of 3M $NH_4OAc$, 5 μL of linear polyacrylamide, and 700 μL of absolute ethanol were added. The solutions were vortexed and placed at −20° C. overnight. Samples were centrifuged at 14000 rpm at 4° C. for 30 minutes. The ethanol was removed, and the samples were allowed to dry for 10 minutes. The cDNA was resuspended in 10–12 μL of PCR grade water.

Polymerase Chain Reaction (PCR). A master mix using the Advantage 2 PCR kit (Ambion) was made for the PCR reactions containing 37–38 μL of PCR grade water, 5 μL of 10× PCR buffer, 1 μL of dNTPs, 1 μL of β-actin primers (10 μM, optional control), and 2 μL of test primers (10 μM, P2Y$_2$, vascular endothelial growth factor (VEGF) or estrogen receptor alpha (ER-α)). Two microliters of cDNA and 1 μL of DNA polymerase were added. Cycling conditions were as follows: 5 min at 95° C.; 25–30 cycles (30 sec at 95° C., 1 min at 63 or 65° C., 3 min at 68° C.); 5 min at 68° C. PCR primers used were as

```
P2Y2-specific primers
(yielding a PCR product of 650 bp):
coding strand:
5'-TGTCTTCGCCCTCTGCTTCC-3';         (SEQ ID NO:1)

noncoding strand:
5'-GTCAGGCCAGGGGTGTCATT-3'.         (SEQ ID NO:2)

β-actin-specific primers (PCR product 300 bp):
coding strand:
5'-AGTCGGTTGGAGCGAGCATC-3';         (SEQ ID NO:3)

noncoding strand:
5'-GGGCACGAAGGCTCATCATT-3'.         (SEQ ID NO:4)

Estrogen receptor alpha (ER-α) specific primers
(PCR product 650 bp):
coding strand:
5'-GGCTGCAAGGCCTTCTTCAA-3';         (SEQ ID NO:5)

noncoding strand:
5'-CATGCGGAACCGAGATGATG-3'.         (SEQ ID NO:6)

Vascular endothelial growth factor (VEGF)
specific primers (PCR product 750 bp):
coding strand:
5'-GCCACCACACCATCACCATC-3';         (SEQ ID NO:10)

noncoding strand:
5'-CCCAAAGCACAGCAATGTCC-3'.         (SEQ ID NO:7)

Mucin-4 (MUC-4) specific primers
(PCR product 800 bp):
coding strand:
5'-AGCCCAGGACTGTGGTCTGC-3';         (SEQ ID NO:8)

noncoding strand:
5'-GCTCACGTTCAGGGCTGTCA-3'.         (SEQ ID NO:9)
```

EXAMPLE 2

Vitamin A Effects Cervical Cell Growth and Gene Expression

The interaction of ME-180 cervical cells with several concentrations of vitamin A derivatives were studied to determine if the vitamin A derivatives would affect ME-180 cellular growth and gene expression.

Figure 2A:
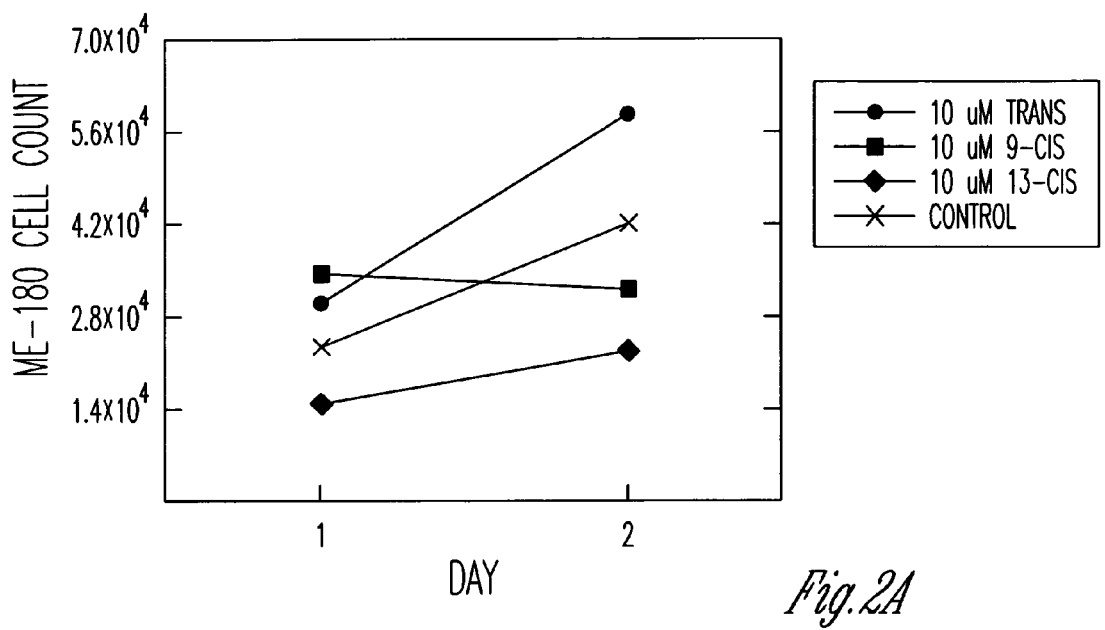
FIG. 2a graphically illustrates the effects of 10 µM trans-retinoic acid (circles), 9-cis-retinoic acid (squares), and 13-cis-retinoic acid (diamonds) on ME-180 cell growth over a period of two days.
Figure 2B:
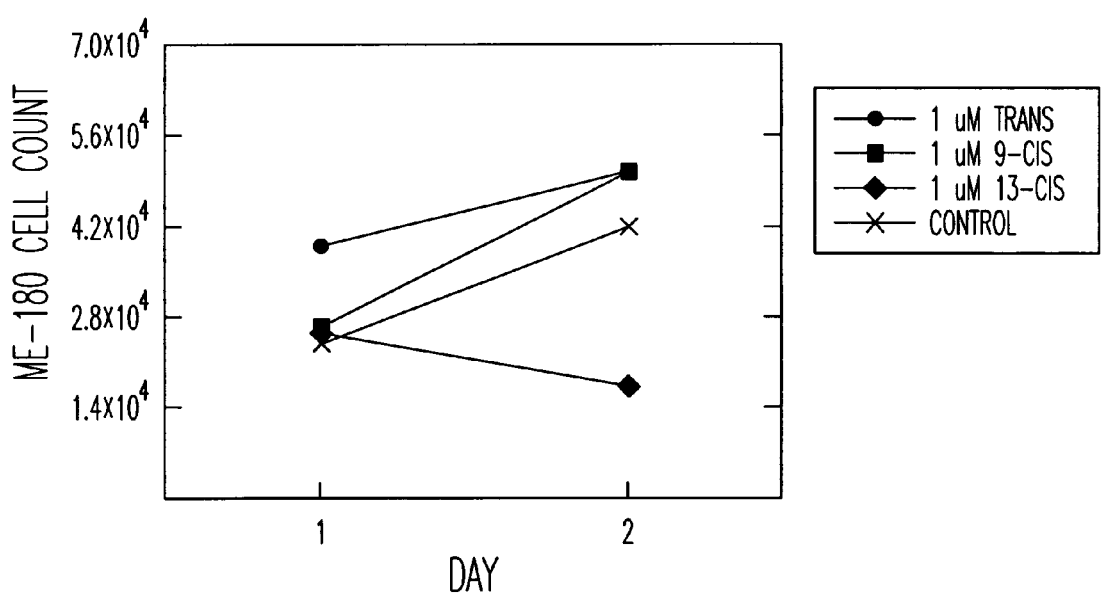
FIG. 2b graphically illustrates the effects of 1 µM trans-retinoic acid (circles), 9-cis-retinoic acid (squares), and 13-cis-retinoic acid (diamonds) on ME-180 cell growth over a period of two days.
Figure 2C:
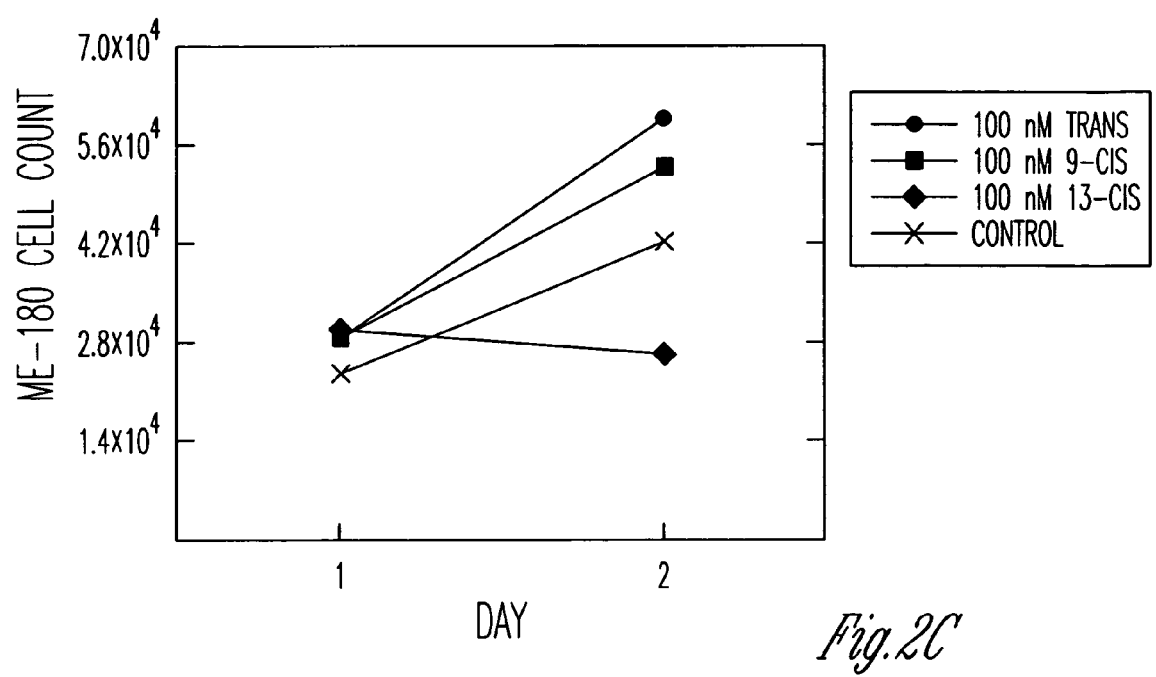
FIG. 2c graphically illustrates the effects of 100 nM trans-retinoic acid (circles), 9-cis-retinoic acid (squares), and 13-cis-retinoic acid (diamonds) on ME-180 cell growth over a period of two days. The number of ME-180 cells is provided on the y-axes.
Figure 3:
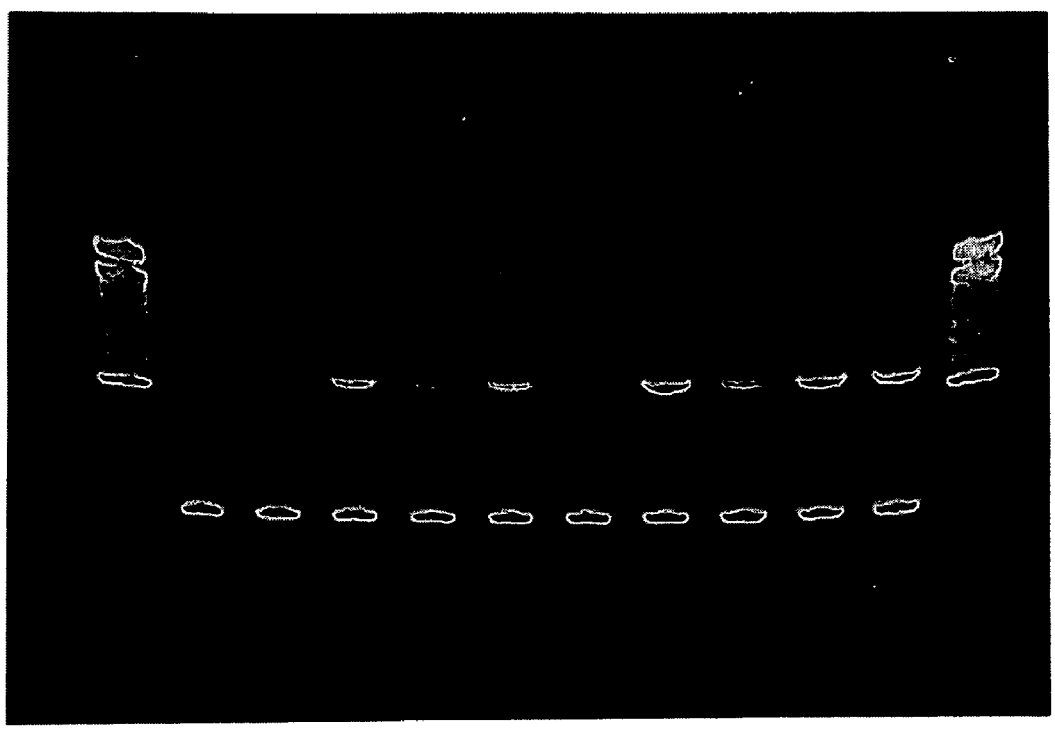
FIG. 3 provides a photograph of an ethidium bromide-stained 2% agarose gel of PCR products using cDNA derived from ME-180 cervical epithelial cell mRNA as template. Two sets of primers were used to generate the products in lanes 2–11: $P2Y_2$-specific primers (top band, 650 bp, lanes 2–11) and β-actin-specific primers (bottom band, 300 bp). Lanes 1 and 12 are DNA size markers. The $P2Y_2$ product can barely be seen in lanes 2, 3, and 7 where the template cDNA was from cervical cells (lane 2), ME-180 cells without vitamin A (lane 3), and ME-180 cells without vitamin A or serum (lane 7), respectively. The addition of 100 nM vitamin A to ME-180 cells caused an increase in $P2Y_2$ expression in the presence of serum (lanes 4–6) and in the absence of serum (lanes 8–11).

Cell Proliferation of ME-180 Cells. ME-180 cells were incubated with vitamin A derivatives for a period of up to 3 days. ME-180 cells were counted on each day. The results of these experiments are shown in FIGS. 2 and 3.

Figure 1B:
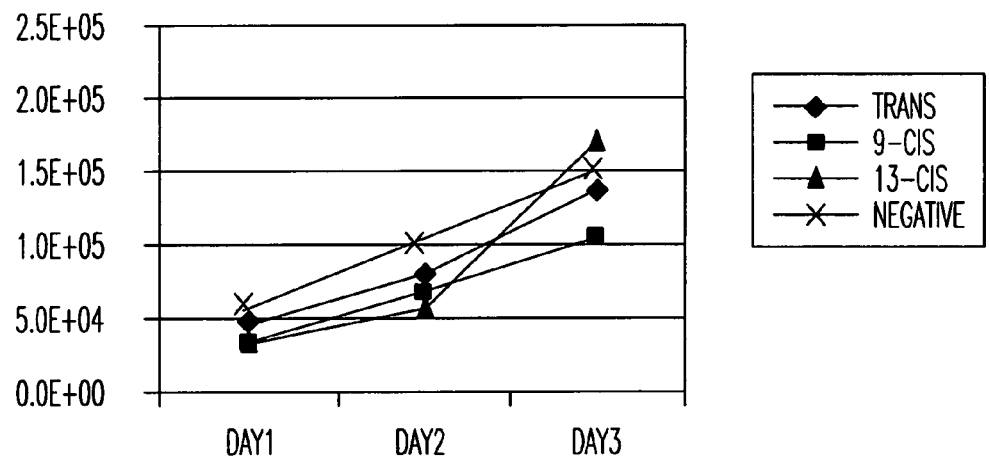
FIG. 1b graphically illustrates the effects of 10 nM of trans-retinoic acid (diamond symbols), 9-cis-retinoic acid (square symbols), and 13-cis-retinoic acid (white triangles) on ME-180 cell growth over a period of three days.
Figure 1C:
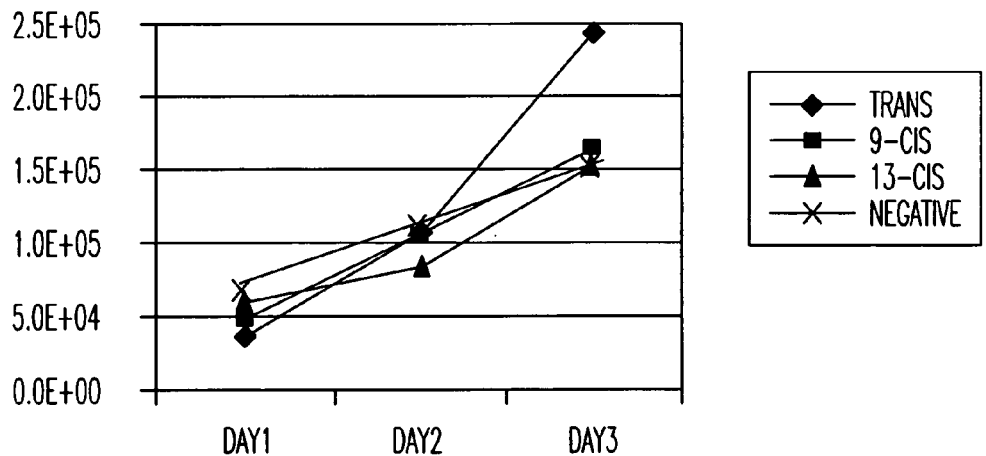
FIG. 1c graphically illustrates the effects of 100 nM of trans-retinoic acid (diamond symbols), 9-cis-retinoic acid (square symbols), and 13-cis-retinoic acid (white triangles) on ME-180 cell growth over a period of three days. The number of ME-180 cells are provided on the y-axes, where E+05 means $10^5$, E+04 means $10^4$ and E+00 means $10^0$.

The data in FIG. 1 indicate that little effect on cell growth is observed using very low concentrations of vitamin A. For example, concentrations of 0.0 nM (negative control), 1 nM, 10 nM, and 100 nM trans-retinoic acid, 9-cis-retinoic acid or 13-cis-retinoic acid had little effect on cell growth. However, cells exposed to trans-retinoic acid appeared to be growing slightly faster than cells exposed to other agents or to no agents (unexposed, negative control cells).

Therefore, another experiment using retinoic acid concentrations ranging from 100 nM to 10 µM was performed. As illustrated in FIG. 2, more cells were present after treatment with 1 µM or 10 µM trans-retinoic acid than after treatment with no retinoic acid (negative control). These data indicate that trans-retinoic acid enhances ME-180 cell growth in culture. In contrast, cells treated with 13-cis-retinoic acid did not grow as well as the negative control, indicating that 13-cis-retinoic acid is toxic to ME-180 cells at micromolar concentrations.

Expression Assay Using Polymerase Chain Reaction and ME-180 cDNA. RNA was isolated from ME-180 cells that had been treated with 1 µM or 10 nM trans-retinoic acid (vitamin A) for 24 hours. After precipitation, the RNA was used as a template for DNA synthesis by reverse transcription as described above. PCR techniques were then used to amplify the newly synthesized DNA to determine the approximate level of transcription of the $P2Y_2$ receptor gene (an approximate 600 bp PCR product). "House-keeping genes" or genes that remain at a constant expression level were also amplified by PCR for comparison. The house-keeping genes tested with $P2Y_2$ was β-actin (~300 bp product).

As shown in FIG. 3, addition of control β-actin primers leads to synthesis of an approximate 300 bp cDNA product that is present in approximately equal amounts in all samples. This result indicates that approximately the same amounts of template RNA were present in all samples. However, as is also illustrated in FIG. 3, the $P2Y_2$ product can barely be seen in lanes 2, 3, and 7 (cervical cDNA control, ME-180 cells without vitamin A, and ME-180 cells without vitamin A or serum, respectively). Thus, in the absence of vitamin A, little $P2Y_2$ mRNA is present in ME-180 cells.

However, upon addition of 100 nM vitamin A to ME-180 cells, an increase in $P2Y_2$ expression is observed both in the presence of serum (FIG. 3, lanes 4–6) and in the absence of serum (FIG. 3, lanes 8–11) in the media. These data indicate that low concentrations of vitamin A may be useful in the treatment of atrophic vaginitis.

Figure 4:
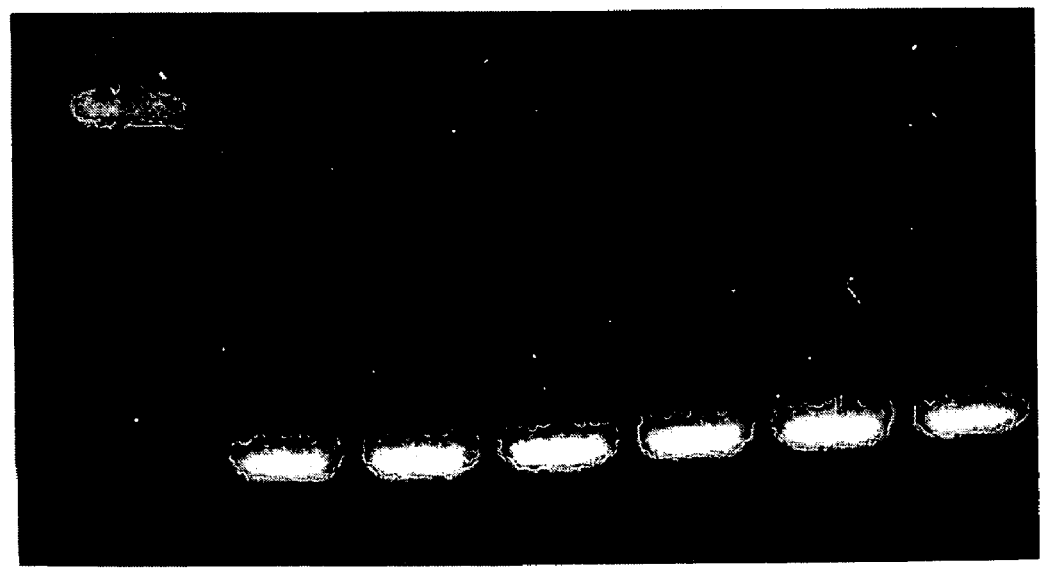
FIG. 4 provides a photograph of an ethidium bromide-stained 2% agarose gel of PCR products using cDNA derived from ME-180 cervical epithelial cells as template. Lane 1 provides DNA size markers. Two sets of primers were used to generate the PCR products in lanes 2–10: ER-α-specific primers (upper band) and β-actin-specific primers (lower band). In Lane 2 the template was cDNA from ME-180 cells cultured in the presence of serum. In Lanes 3 and 7, the template was cDNA from ME-180 cells cultured in the absence of serum. In Lanes 4–6, the templates were cDNAs from ME-180 cells cultured without serum and treated with 100 nM vitamin A for 4, 8 and 16 hours, respectively. Addition of 100 nM vitamin A to ME-180 cells caused an increase in ER-α expression.

Cell samples exposed to vitamin A in the absence of serum were also tested for expression of other genes that may also affect atrophic vaginitis. Using primers designed to amplify the estrogen receptor alpha (ER-α) gene, PCR was performed using the RNA samples from cells starved of serum. The ER-α product (650 bp) was visible in the control (FIG. 4, lane 2), where the template was cDNA from ME-180 cells cultured in the presence of serum. In samples that did not contain serum or vitamin A, the cDNA fragment signifying ER-α gene expression was not detected (lanes 3 and 7, FIG. 4). However, in the samples that were exposed to 100 nM vitamin A but no serum for 4, 8, and 16 hours, the ER-α gene was expressed (Lanes 4–6, respectively). These data indicate that vitamin A can induce the expression of ER-α in cervical epithelial cells cultured in the absence of serum. Increasing the amount of estrogen receptors on epithelial cells in the genital tract may increase the probability that a receptor will be activated by estrogen.

Figure 5:
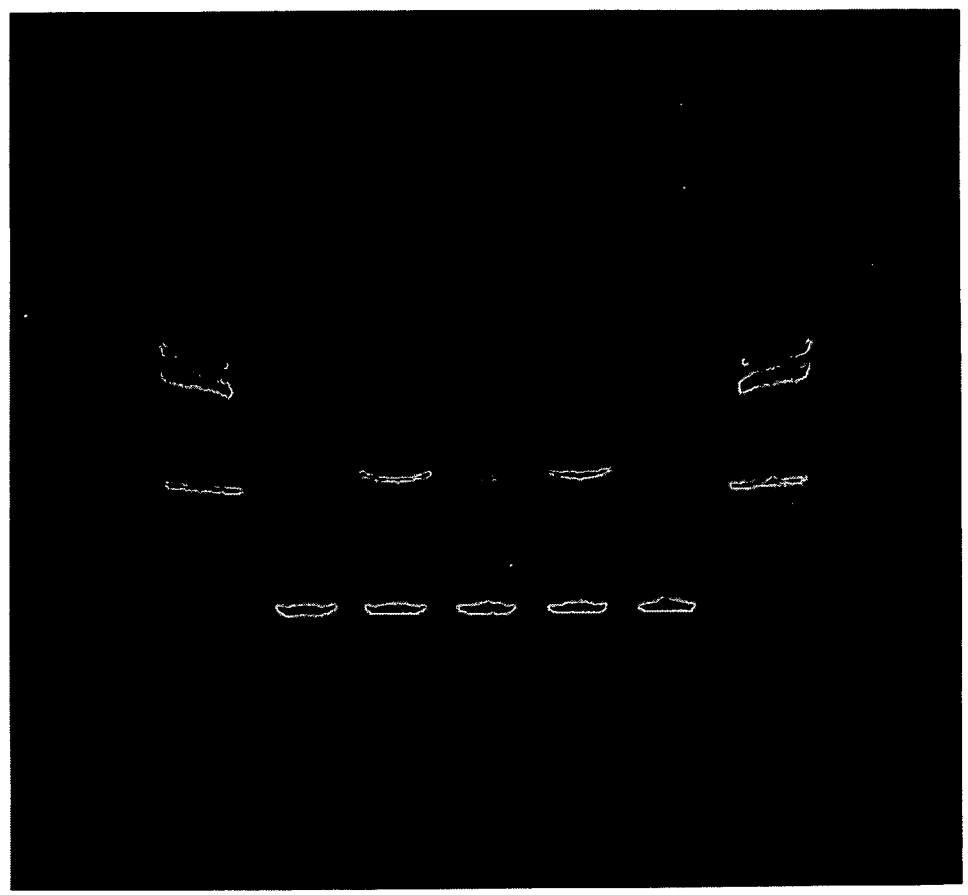
FIG. 5 provides a photograph of an ethidium bromide-stained 2% agarose gel of PCR products using RNA from various cell types as template. Lanes 1 and 7 provide DNA size markers. Two sets of primers were used to generate the PCR products in lanes 2–6: vascular endothelial growth factor (VEGF) specific primers (upper band) and β-actin-specific primers (lower band). Lanes 2 and 6 provide the PCR products from cDNA derived from untreated ME-180 cells. Lanes 3–5 provide the PCR products from cDNA derived from ME-180 cells treated with 100 nM vitamin A for 4, 8, and 16 hours, respectively.

Moreover, treatment of ME-180 cells with 100 nM vitamin A also increased the expression of vascular endothelial growth factor (VEGF), an important factor involved in blood vessel formation. As illustrated in FIG. 5, an approximate 700 bp product characteristic of VEGF is detected in ME-180 cells treated with 100 nM vitamin A.

These experiments indicate that vitamin A (trans-retinoic acid) is nontoxic and may be useful for enhancing natural vaginal moisture for women suffering from atrophic vaginitis. Vitamin A increases cervical cell growth at micromolar concentrations, which could help to strengthen vaginal tissue. The presence of vitamin A increases the expression of estrogen receptor alpha, vascular endothelial growth factor and the $P2Y_2$ receptor gene in cervical epithelial cells. Such increases in expression may help to treat the symptoms of atrophic vaginitis.

EXAMPLE 3

Vitamin A Increases Mucin-4 Expression

Materials and Methods

RNA was isolated (as described above) from ME-180 cervical cells treated with 0 nM or 100 nm vitamin A in the absence of serum. The RNA was reverse transcribed to form cDNA, and PCR techniques (as described above) were used to determine the effect of vitamin A on the expression of mucin-4 (MUC-4).

Results

Figure 6:
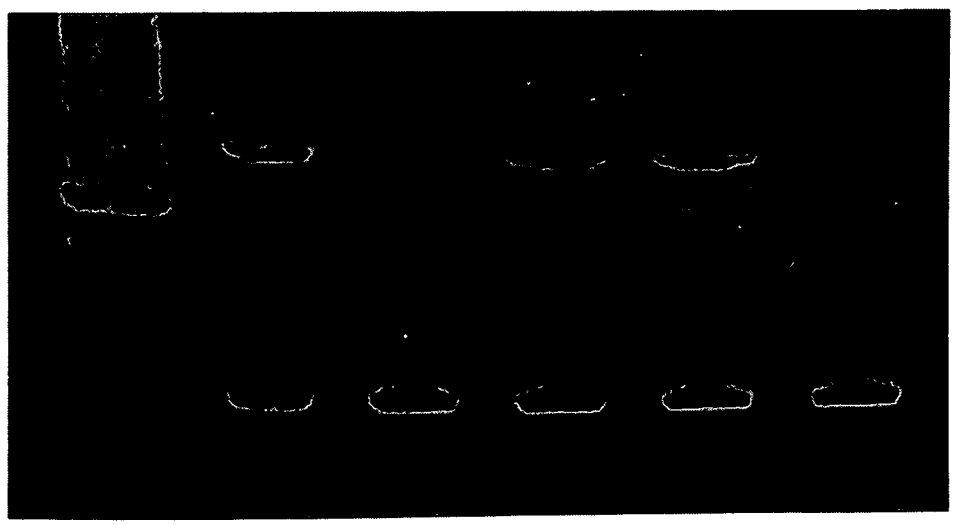
FIG. 6 provides a photograph of an ethidium bromide-stained 2% agarose gel of PCR products using RNA from various cell types as template. Lane 1 of the gel depicted in FIG. 6 contains DNA size markers, in particular a 100 bp ladder of size markers (the brightest band is 600 bp). Lane 2 contains the products of RT-PCR reaction using template cDNA derived from cervical RNA and mucin-4 primers (800 bp product) with β-actin primers (300 bp product). Lane 3 contains the same PCR reaction using template cDNA from ME-180 cells. Lane 4 contains the same PCR reaction using template cDNA from ME-180 cells treated with 100 nM vitamin A for 24 hours.

As shown in FIG. 6, addition of control β-actin primers leads to synthesis of a 300 bp DNA product that is present in approximately equal amounts in all samples. This result indicates that approximately the same amounts of template RNA were present in all samples. However, as is also illustrated in FIG. 6, the MUC-4 product (800 bp) is found in the cervical cDNA control (lane 2). In ME-180 cells without vitamin A (lane 3), the MUC-4 product is absent. However, upon addition of 100 nM vitamin A to ME-180 cells, MUC-4 expression is detectable after 4 hours or 8 hours of treatment (lanes 4 and 5, respectively). After 16 hours of treatment with 100 nM vitamin A (lane 6), MUC-4 expression decreases but is still detectable. These data indicate that low concentrations of vitamin A may be useful in the treatment of atrophic vaginitis by increasing the expression of MUC-4.

REFERENCES

These references and the other references cited herein are incorporated by reference in their entirety.

U.S. Pat. No. 6,264,975 entitled, "Methods of hydrating mucosal surfaces."

U.S. Pat. Nos. 5,981,506; 5,972,904; 5,958,897; 5,789,391 entitled, "Method of treating sinusitis with UTPs and other related compounds."

U.S. Pat. No. 6,277,855 entitled, "Method of treating dry eye disease with nicotinic acetylcholine receptor agonists."

U.S. Pat. No. 6,200,981 entitled, "Pyrimidine derivatives."

U.S. Pat. No. 6,107,091 entitled, "Antisense inhibition of G-alpha-16-expression."

U.S. Pat. No. 5,837,861 entitled, "Dinucleotides and their use as modulators of mucociliary clearance and ciliary beat frequency."

U.S. Pat. No. 5,985,849 entitled, "Phosphate compounds and their use as medicaments."

U.S. Pat. No. 6,107,297 entitled, "2,4-Dithi(oxo)-pyrimidin-5-yl compounds bearing a tricyclic substituent useful as P2 purinoceptor antagonists."

Garrad, R. C., Otero, M. A., Erb, L., Theiss, P. M., Clarke, L. L., Gonzalez, F. A., Turner, J. T., Weisman, G. A. "Structural basis of agonist-induced desensitization and sequestration of the P2Y$_2$ nucleotide receptor," Journal of Biological Chemistry 1998, 273 (45), 29437–29444

Gorodeski, G. I., Burfiend, P., Gan, S. U., Pal, D., Abdul-Karim, F. W. "Regulation by retinoids of P2Y$_2$ nucleotide receptor mRNA in human uterine cervical cells," American Journal of Physiology 1998, C758–C765

What is claimed:

1. A method of preventing or treating vaginal dryness in a mammal in need of such prevention or treatment comprising administering to the vaginal cavity an effective amount of a composition comprising a retinoid or a carotenoid, a nucleotide or a nucleoside, and a pharmaceutically acceptable excipient for use in the vaginal cavity area.

2. The method of claim 1, wherein the retinoid or carotenoid is a compound of Formula IA or IB:

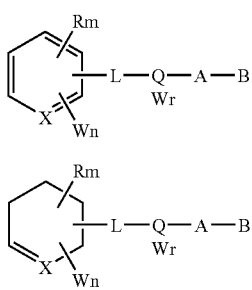

wherein:
X is CH, or N;
R is H or alkyl of 1 to 6 carbons;
m is an integer having the value of 0–5;
n is an integer having the value of 0–2;
r is an integer having the value 0–2;

L is —(C=Z)—NH— or —NH—(C=Z)— where Z is O or S;

Q is a phenyl, naphthyl, pyridyl, thienyl, furyl, pyridazinyl, pyrimidinyl, pyrazinyl, thiazolyl, oxazolyl, imidazolyl or pyrrazolyl, wherein the phenyl, naphthyl pyridyl, thienyl, furyl, pyridazinyl, pyrimidinyl, pyrazinyl, thiazolyl, oxazolyl, imidazolyl or pyrrazolyl group can be substituted with one or two $R^1$ groups;

W is F, Br, Cl, I, $C_{1-6}$ alkyl, fluoro-substituted $C_{1-6}$ alkyl, $NO_2$, $N_3$, OH, $OCH_2OCH_3$, O—$C_{1-10}$ alkyl, tetrazol, CN, $SO_2C_{1-6}$-alkyl, $SO_2C_{1-6}$-fluoro-substituted alkyl, SO—$C_{1-6}$ alkyl, CO—$C_{1-6}$alkyl, $COOR_8$, phenyl, phenyl itself substituted with a W group other than with phenyl or substituted phenyl, with the proviso that when X is CH and r is 0 then n is not 0 and at least one W group is not alkyl;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; and B is COOH, $COOR^8$, $CONR^9R^{10}$, $CH_2OH$, $CH_2OR^{11}$, $CH_2OCOR^{11}$, CHO, $CH(OR^{12})_2$, $CHOR^{13}O$, $COR^7$, $CR^7(OR^{12})_2$, $CR^7OR^{13}O$, where $R^7$ is an alkyl, cycloalkyl or alkenyl group containing 1 to 5 carbons, $R^8$ is an alkyl group of 1 to 10 carbons or trimethylsilylalkyl where the alkyl group has 1 to 10 carbons, or a cycloalkyl group of 5 to 10 carbons, or $R^8$ is phenyl or lower alkylphenyl, $R^9$ and $R^{10}$ independently are hydrogen, an alkyl group of 1 to 10 carbons, or a cycloalkyl group of 5–10 carbons, or phenyl or lower alkylphenyl, $R^{11}$ is lower alkyl, cycloalkyl, lower alkyl substituted cycloalkyl, phenyl or lower alkylphenyl, $R^{12}$ is lower alkyl, and $R^{13}$ is divalent alkyl radical of 2–5 carbons; or a pharmaceutically acceptable salt thereof.

3. The method of claim 1, wherein the retinoid or carotenoid is a compound of Formula II:

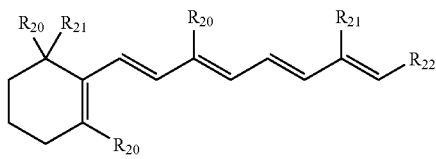

wherein:

$R_{20}$, $R_{21}$ and $R_{22}$ are each independently $C_{1-6}$ alkyl, fluoro-substituted $C_{1-6}$ alkyl, hydroxy-substituted $C_{1-6}$ alkyl, $CH_2OH$, $CH_2OR^{11}$, $CH_2OCOR^{11}$, CHO, $CH(OR^{12})_2$, $CHOR^{13}O$, $COR^7$, $CR^7(OR^{12})_2$, or $CR^7OR^{13}O$, where $R^7$ is an alkyl, cycloalkyl or alkenyl group containing 1 to 5 carbons, $R^{11}$ is lower alkyl, cycloalkyl, lower alkyl substituted cycloalkyl, phenyl or lower alkylphenyl, $R^{12}$ is lower alkyl, and $R^{13}$ is divalent alkyl radical of 2–5 carbons; or a pharmaceutically acceptable salt thereof.

4. The method of claim 1, wherein the retinoid or carotenoid is vitamin A, beta-carotene, retinal, retinoic acid or retinol.

5. The method of claim 1, wherein the nucleotide or nucleoside is a compound of Formula III:

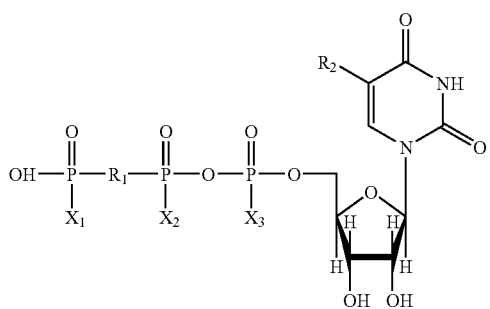

wherein:

$X_1$, $X_2$ and $X_3$ are each independently either $O^-$ or $S^-$;

$R_1$ is O, imido, methylene, or dihalomethylene; and $R_2$ is H or Br; or a pharmaceutically acceptable salt thereof.

6. The method of claim 1, wherein the nucleotide or nucleoside is dATP, ATP, dGTP, GTP, dCTP, CTP, dTTP, TTP, dUTP or UTP.

7. The method of claim 1, wherein the effective amount comprises about 0.01 milligrams to about 1 milligrams retinoid or carotenoid.

8. The method of claim 1, wherein the effective amount comprises about 0.1 micromolar to about 100 micromolar retinoid or carotenoid.

9. The method of claim 1, wherein the composition comprises a lotion, cream gel, spray, foam or vaginal insert.

10. A composition for increasing mucus secretion in the female reproductive tract comprising an effective amount of a retinoid or a carotenoid, an effective amount of a nucleotide or nucleoside, and a pharmaceutically acceptable excipient for use in the vaginal cavity area.

11. The composition of claim 10, wherein the retinoid or the carotenoid is a compound of Formula IA or IB:

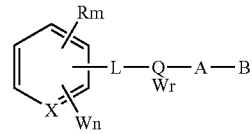

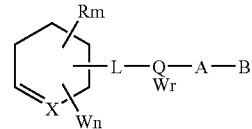

wherein:

X is CH, or N;

R is H or alkyl of 1 to 6 carbons;

m is an integer having the value of 0–5;

n is an integer having the value of 0–2;

r is an integer having the value 0–2;

L is —(C=Z)—NH— or —NH—(C=Z)— where Z is O or S;

Q is a phenyl, naphthyl, pyridyl, thienyl, furyl, pyridazinyl, pyrimidinyl, pyrazinyl, thiazolyl, oxazolyl, imidazolyl or pyrrazolyl, wherein the phenyl, naphthyl pyridyl, thienyl, furyl, pyridazinyl, pyrimidinyl, pyrazinyl, thiazolyl, oxazolyl, imidazolyl or pyrrazolyl group can be substituted with one or two $R^1$ groups;

W is F, Br, Cl, I, $C_{1-6}$ alkyl, fluoro-substituted $C_{1-6}$ alkyl, $NO_2$, $N_3$, OH, $OCH_2OCH_3$, $O$—$C_{1-10}$ alkyl, tetrazol, CN, $SO_2C_{1-6}$-alkyl, $SO_2C_{1-6}$-fluoro-substituted alkyl, SO—$C_{1-6}$ alkyl, CO—$C_{1-6}$alkyl, $COOR_8$, phenyl, phenyl itself substituted with a W group other than with phenyl or substituted phenyl, with the proviso that when X is CH and r is 0 then n is not 0 and at least one W group is not alkyl;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; and B is COOH, $COOR^8$, $CONR^9R^{10}$, $CH_2OH$, $CH_2OR^{11}$, $CH_2OCOR^{11}$, CHO, $CH(OR^{12})_2$, $CHOR^{13}O$, $COR^7$, $CR^7(OR^{12})_2$, $CR^7OR^{13}O$, where $R^7$ is an alkyl, cycloalkyl or alkenyl group containing 1 to 5 carbons, $R^8$ is an alkyl group of 1 to 10 carbons or trimethylsilylalkyl where the alkyl group has 1 to 10 carbons, or a cycloalkyl group of 5 to 10 carbons, or $R^8$ is phenyl or lower alkylphenyl, $R^9$ and $R^{10}$ independently are hydrogen, an alkyl group of 1 to 10 carbons, or a cycloalkyl group of 5–10 carbons, or phenyl or lower alkylphenyl, $R^{11}$ is lower alkyl, cycloalkyl, lower alkyl substituted cycloalkyl, phenyl or lower alkylphenyl, $R^{12}$ is lower alkyl, and $R^{13}$ is divalent alkyl radical of 2–5 carbons; or a pharmaceutically acceptable salt thereof.

12. The composition of claim 10, wherein the retinoid or the carotenoid is a compound of wherein the retinoid or carotenoid is vitamin A, beta-carotene, retinal, retinoic acid or retinol.

13. The composition of claim 10, wherein the nucleotide or nucleoside is a compound of Formula III:

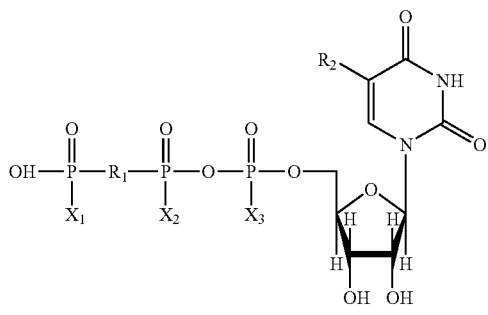

wherein:
$X_1$, $X_2$ and $X_3$ are each independently either $O^-$ or $S^-$;
$R_1$ is O, imido, methylene, or dihalomethylene; and
$R_2$ is H or Br; or
a pharmaceutically acceptable salt thereof.

14. The composition of claim 10, wherein the nucleotide or nucleoside is dATP, ATP, dGTP, GTP, dCTP, CTP, dTTP, TTP, dUTP or UTP.

15. The composition of claim 10, wherein the effective amount comprises about 0.01 milligrams to about 1 milligrams retinoid or carotenoid.

16. The composition of claim 10, wherein the effective amount comprises about 0.1 micromolar to about 100 micromolar retinoid or carotenoid.

17. The composition of claim 10, the composition comprises a lotion, cream gel, spray, or foam.

18. The composition of claim 10, wherein the composition comprises a vaginal insert.

* * * * *